(12) United States Patent
Gross et al.

(10) Patent No.: US 11,051,797 B2
(45) Date of Patent: Jul. 6, 2021

(54) EYELID SPECULUM

(71) Applicant: BioGenware, LLC, Columbia, SC (US)

(72) Inventors: Jeffrey G. Gross, Columbia, SC (US); John Lowsky, Jr., Columbia, SC (US)

(73) Assignee: BioGenware, LLC, Columbia, SC (US)

( * ) Notice: Subject to any disclaimer, the term of this patent is extended or adjusted under 35 U.S.C. 154(b) by 0 days.

(21) Appl. No.: 16/830,576

(22) Filed: Mar. 26, 2020

(65) Prior Publication Data
US 2020/0305858 A1 Oct. 1, 2020

Related U.S. Application Data

(60) Provisional application No. 62/826,287, filed on Mar. 29, 2019.

(51) Int. Cl.
*A61B 17/02* (2006.01)

(52) U.S. Cl.
CPC ...... *A61B 17/0231* (2013.01); *A61B 17/0293* (2013.01); *A61B 2560/04* (2013.01)

(58) Field of Classification Search
CPC ............ A61B 17/0231; A61B 17/0293; A61B 2560/04
USPC ......................................... 600/206, 236, 213
See application file for complete search history.

(56) References Cited

U.S. PATENT DOCUMENTS

| | | | |
|---|---|---|---|
| 3,409,349 A | 11/1968 | Boyle et al. | |
| 5,171,254 A | 12/1992 | Sher | |
| 5,374,272 A | 12/1994 | Arpa et al. | |
| 5,433,190 A | 7/1995 | Sunalp | |
| 5,938,674 A | 8/1999 | Terry | |
| 6,022,365 A | 2/2000 | Aufaure et al. | |
| 6,083,155 A | 7/2000 | Trese | |
| 6,267,752 B1 | 7/2001 | Svetliza | |
| 6,440,065 B1 | 8/2002 | Hered | |
| D489,130 S | 4/2004 | Sinding | |

(Continued)

FOREIGN PATENT DOCUMENTS

| | | |
|---|---|---|
| CN | 101167672 A | 4/2008 |
| CN | 101695460 A | 4/2010 |

(Continued)

OTHER PUBLICATIONS

International Search Report and Written Opinion for PCT/US2020/024822, dated Jun. 22, 2020, 13 pages.

*Primary Examiner* — Eduardo C Robert
*Assistant Examiner* — David C Comstock
(74) *Attorney, Agent, or Firm* — Dority & Manning, P.A.

(57) ABSTRACT

An eyelid speculum, a kit containing the eyelid speculum, and a method of using the eyelid speculum in the diagnosis and/or treatment of a patient are provided. The eyelid speculum includes a central ring having an upper surface, a lower surface, an inner side surface, an outer side surface, a first end, and a second end. The first end and the second end are separated by a gap, and the central ring defines an opening. The eyelid speculum also includes first and second eyelid margin holders that extend outwardly from the outer side surface of the central ring at the first end and second end, respectively, where each eyelid margin holder has an upper portion and a lower portion. In addition, the eyelid speculum includes finger tabs that extend upwardly from the upper portions of the first and second eyelid margin holders.

21 Claims, 8 Drawing Sheets

(56) References Cited

U.S. PATENT DOCUMENTS

| | | | |
|---|---|---|---|
| D498,531 S | 11/2004 | Sinding | |
| 8,066,635 B2 | 11/2011 | Beck | |
| 8,936,550 B2 | 1/2015 | Urano et al. | |
| 9,668,916 B2 | 6/2017 | Thompson | |
| 10,130,351 B2 | 11/2018 | Shugarman | |
| 2007/0270657 A1* | 11/2007 | Stephenson | A61B 1/32 600/236 |
| 2009/0227846 A1* | 9/2009 | Beck | A61B 1/32 600/236 |
| 2012/0071726 A1* | 3/2012 | Beck | A61B 1/32 600/214 |
| 2016/0030239 A1 | 2/2016 | Akura et al. | |

FOREIGN PATENT DOCUMENTS

| | | |
|---|---|---|
| CN | 206597081 U | 10/2017 |
| CN | 108143540 A | 6/2018 |
| CN | 109199692 A | 1/2019 |
| DE | 9320127 U1 | 4/1994 |
| FR | 2827497 A1 | 1/2003 |
| GB | 114051 A | 3/1918 |
| GB | 2 382 779 B | 6/2006 |
| GB | 2507285 B | 11/2016 |
| KR | 101198016 B1 | 11/2012 |
| TW | 200735852 A | 10/2007 |
| WO | WO 2011/077115 A1 | 6/2011 |
| WO | WO 2017/027763 A1 | 2/2017 |
| WO | WO 2018198686 A1 | 11/2018 |

\* cited by examiner

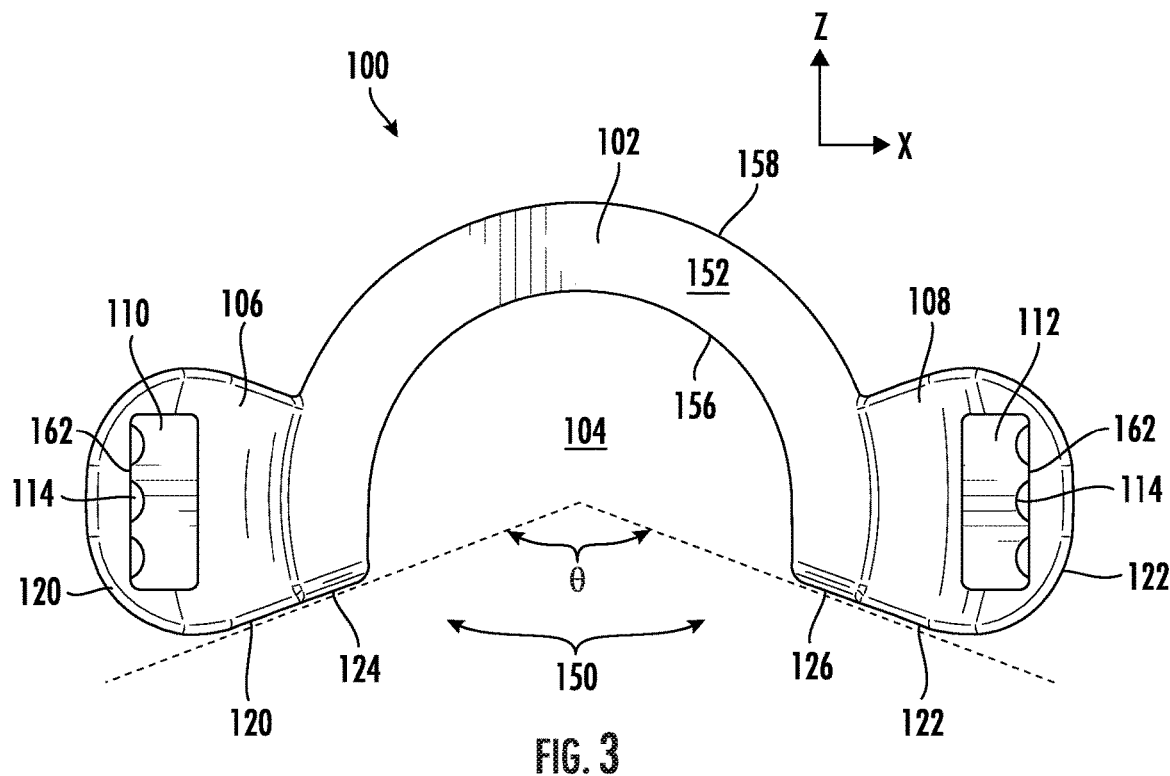
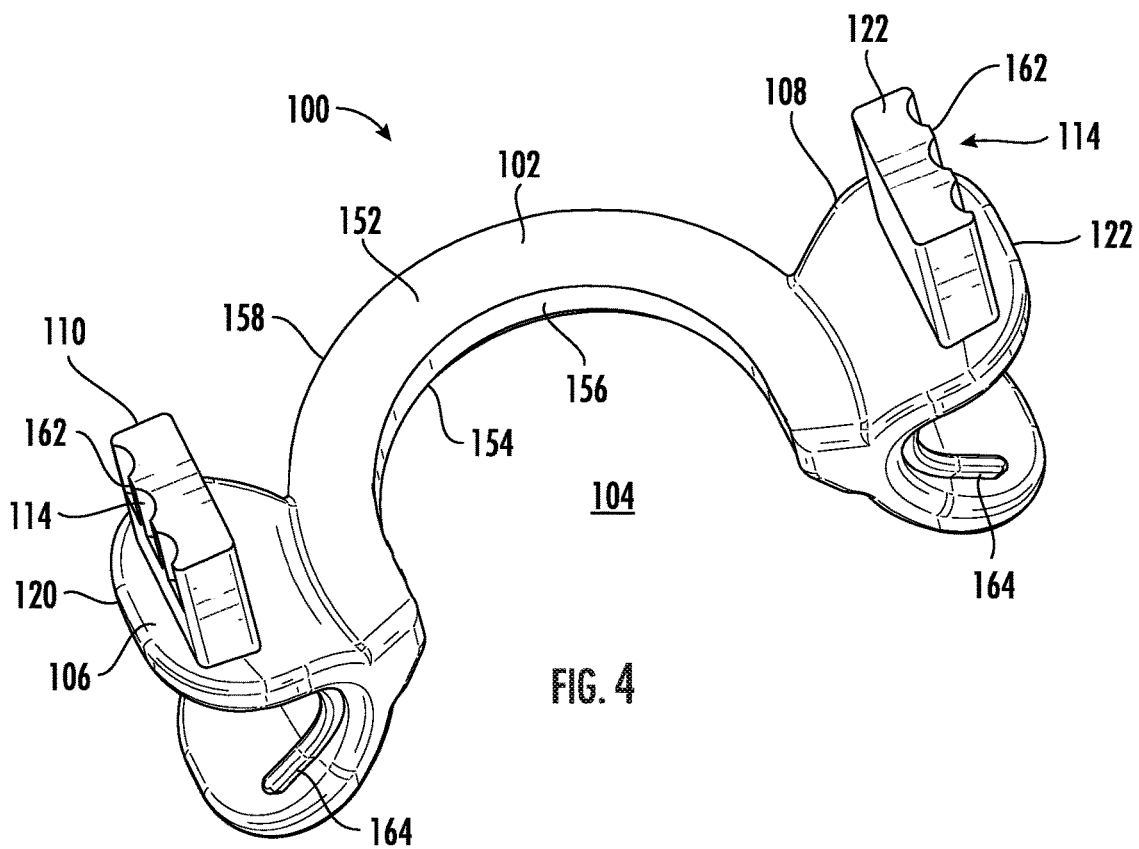

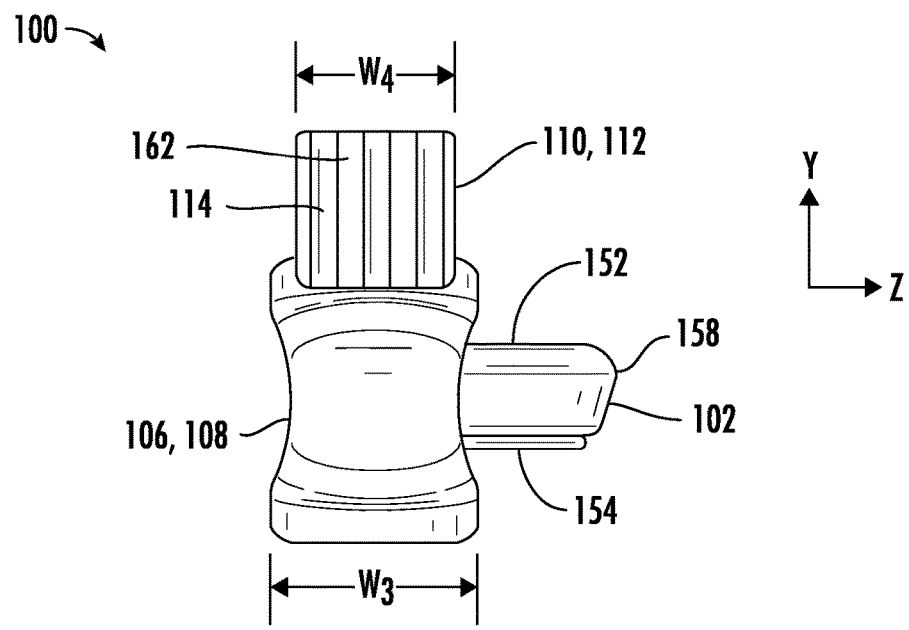
FIG. 5
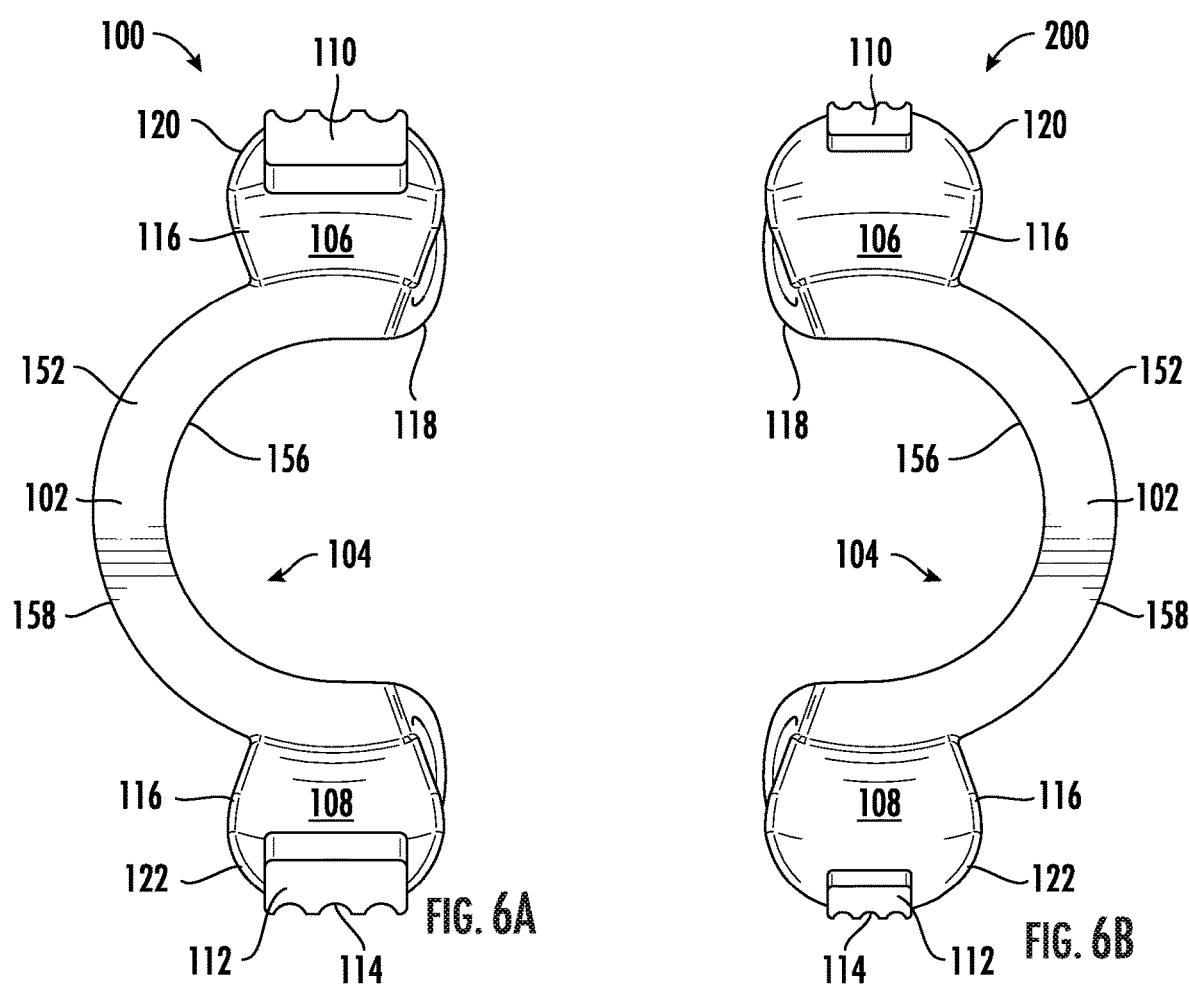
FIG. 6A
FIG. 6B

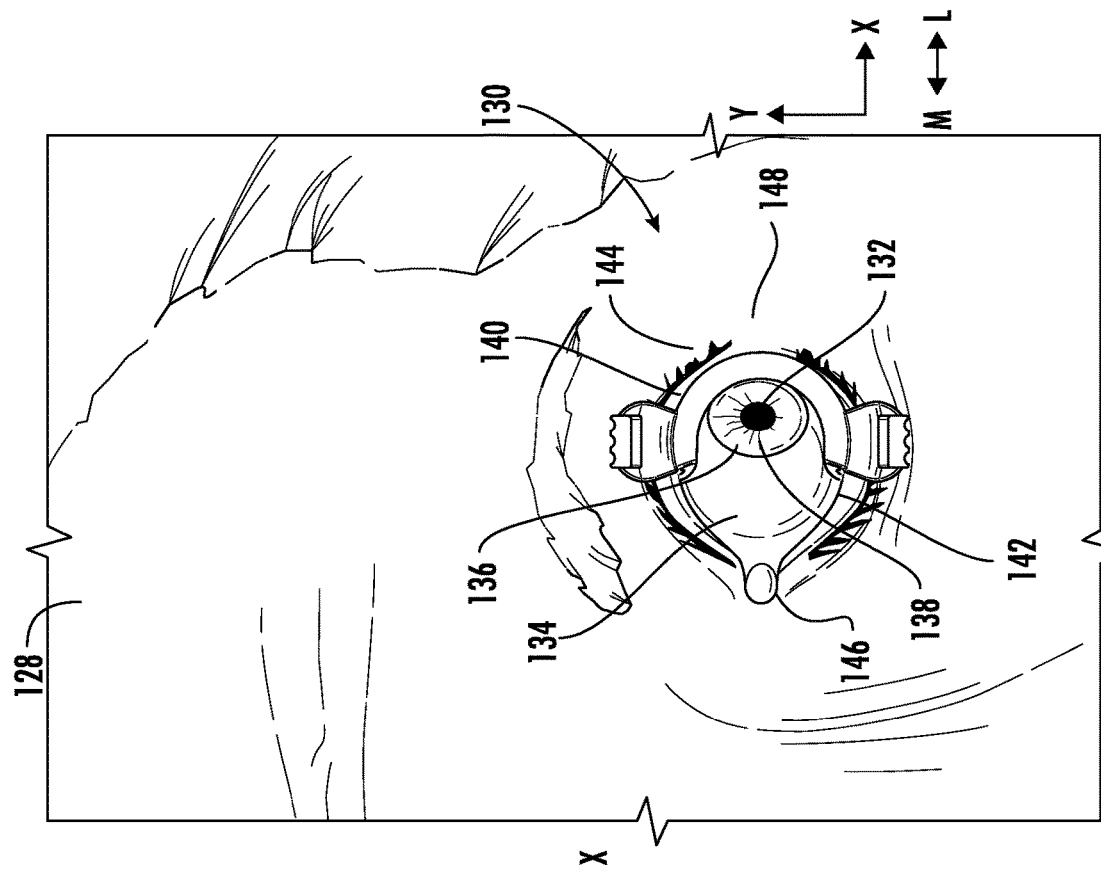
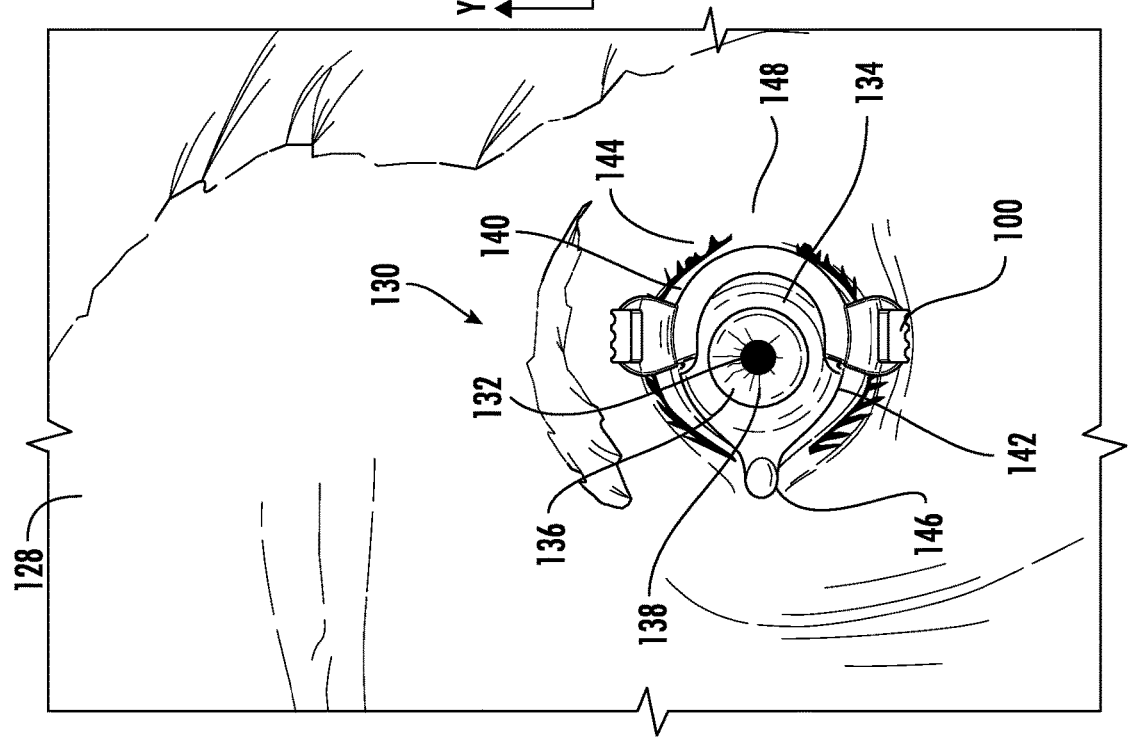

EYELID SPECULUM

CROSS-REFERENCE TO RELATED APPLICATIONS

The present application claims priority to U.S. Patent Application Ser. No. 62/826,287, filed on Mar. 29, 2019, the entire contents of which are incorporated herein by reference.

BACKGROUND OF THE INVENTION

The traditional eyelid speculum is one of the most commonly used devices in ophthalmology. For example, recent surveys indicate that physicians in the United States use a traditional eyelid speculum at least 75% of the time when performing intravitreal injections, and the number of intravitreal injections performed yearly to treat conditions such as macular degeneration, diabetic retinopathy, and retinal vein occlusions, among other conditions, is estimated to be approximately 6 million in the United States and 22 million worldwide. One particular example of a traditional eyelid speculum is known by those in the art as the Barraquer speculum. The Barraquer speculum includes open or solid wire loops that are designed to retract the eyelids during ophthalmic surgery or minor office procedures, such as during eye injections. The purpose of an eyelid speculum is to retract the eyelids of a patient to allow for consistent exposure for surgical maneuvers, intravitreal injections, imaging procedures, and the like. The Barraquer speculum is typically formed of metal and wire and is a large device that is often intimidating to patients, with many patients finding the insertion of the Barraquer speculum to be more uncomfortable than the surgery or office procedure that follows. Moreover, the Barraquer speculum is not disposable and must be autoclaved for sterile reuse, where there is a risk that the Barraquer speculum may not be sterile if the autoclave procedure is not conducted properly. Another instrument that may be used is the Desmarres or Jaffe eyelid retractor, but, like the Barraquer speculum, it is often formed from metal, is not disposable, and must be autoclaved before reuse. Therefore, it shares many of the disadvantages of the Barraquer speculum.

As an alternative, some physicians opt to manually retract a patient's eyelids without the use of a speculum. Although many patients indicated this is more comfortable than eyelid retraction via a Barraquer speculum, manual retraction may not provide the safety to adequately expose an injection site and may not prevent contact of an instrument (e.g., a needle) with a patient's eyelashes, which puts the patient at risk for developing an infection. Further, involuntary eyelid closure during injections has been shown to lead to increased levels of needle contamination when no eyelid speculum is used As such, a need currently exists for an eyelid speculum that is more comfortable to the patient and that is easily insertable by the physician, health care provider, or assistant. An economical, disposable eyelid speculum would also be useful.

SUMMARY OF THE INVENTION

In accordance with one exemplary embodiment of the present invention, an eyelid speculum is provided.

According to one particular embodiment of the present invention, an eyelid speculum is provided. The eyelid speculum includes a central ring having an upper surface, a lower surface, an inner side surface, an outer side surface, a first end, and a second end. The first end and the second end are separated by a gap, and the central ring defines an opening. The eyelid speculum also includes a first eyelid margin holder extending outwardly from the outer surface of the central ring at the first end and having an upper portion and a lower portion, a second eyelid margin holder extending outwardly from the outer surface of the central ring at the second end and having an upper portion and a lower portion, a first finger tab extending upwardly from the upper portion of the first eyelid margin holder, and a second finger tab extending upwardly from the upper portion of the second eyelid margin holder.

In one embodiment, an angle formed between the first end and the second end can range from about 120° to about 185°.

In another embodiment, the central ring can be c-shaped or semicircular.

In still another embodiment, the first eyelid margin-holder and the second eyelid margin holder can be c-shaped or semicircular.

In yet another embodiment, the upper portions and the lower portions of the first eyelid margin holder and the second eyelid margin holder can extend from the outer side surface of the central ring.

In an additional embodiment, the upper portions and the lower portions of the first eyelid margin holder and the second eyelid margin holder can be curved.

In one more embodiment, the upper portion and the lower portion of the first eyelid margin holder can be separated by a central portion and the upper portion and the lower portion of the second eyelid margin holder can be separated by a central portion. Further, the central portion of the first eyelid margin holder and the central portion of the second eyelid margin holder can each contact the outer side surface of the central ring.

In another embodiment, the first finger tab and the second finger tab can each include a textured outer surface. Further, the textured outer surface can include a plurality of ridges.

In still another embodiment, the first eyelid margin holder can be configured for positioning around an upper eyelid and the second eyelid margin holder can be configured for positioning around a lower eyelid.

In yet another embodiment, the central ring can be free from contact with an outer surface of an eye of a patient when the eyelid speculum is used to retract an eyelid of the patient.

In an additional embodiment, the eyelid speculum can be formed from a thermoplastic polymer. Further, the thermoplastic polymer can include acrylonitrile butadiene styrene, polyethylene, polypropylene, polycarbonate, polyamide, polystyrene, polymethyl methacrylate, or a combination thereof.

In one more embodiment, the eyelid speculum can be disposable after a single use.

In another embodiment, the eyelid speculum can include an attachment, where the central ring can include a first mating component and the attachment can include a second mating component, where the central ring and the attachment can be connected by the first mating component and the second mating component.

In another particular embodiment of the present invention, a kit comprising the eyelid speculum described above and a medication delivery system is also provided. Further, the eyelid speculum and the medication delivery system can be contained within a sterilized package. In addition, the kit can also include a medication.

In still another particular embodiment of the present invention, a method for separating a first eyelid and a second eyelid from an outer surface of an eye is provided. The method can include the step of inserting the eyelid speculum into an eye of a patient, where the lower surface of the central ring is positioned adjacent yet does not contact the outer surface of the eye, where the first eyelid margin holder is positioned at an inner corner of the eye and the second eyelid margin holder is positioned at an outer corner of the eye. The method can also then include the step of rotating the eyelid speculum in a first direction by about 75° to about 115° via the first finger tab and the second finger tab by about 75° to about 115° such that the first eyelid is positioned between the upper portion and the lower portion of the first eyelid margin holder and the second eyelid is positioned between the upper portion and the lower portion of the second eyelid margin holder. Such an angle allows for a more controlled, safer, and comfortable insertion mechanism than the traditional wire speculum and may avoid the inadvertent corneal trauma sometimes associated with the metal lid holders found in traditional wire speculums.

In another embodiment, the method can also include the steps of performing a desired diagnostic or treatment procedure and removing the eyelid speculum by rotating the eyelid speculum in a second direction that is opposite the first direction by about 75° to about 115° via the first finger tab and the second finger tab such that the first eyelid margin holder is positioned at an inner corner of the eye and the second eyelid margin holder is positioned at an outer corner of the eye and lifting the eyelid speculum away from the outer surface of the eye.

Other features and aspects of the present invention are set forth in greater detail below.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which:

FIG. 3 is a top view of the eyelid speculum of the present invention;

FIG. 4 is a perspective view of another embodiment of the eyelid speculum of the present invention;

FIG. 5 is a side view of the eyelid speculum of the present invention;

FIG. 6A is a top view of one embodiment of the eyelid speculum of the present invention;

FIG. 6B is a top view of another embodiment of the eyelid speculum of the present invention;

FIG. 8B illustrates the eyelid speculum of the present invention after it has been rotated into the desired position in order to separate the upper eyelid and lower eyelid of the patient;

FIG. 8C illustrates the ability of the patient to move the eye medially and laterally after the eyelid speculum of the present invention has been inserted into the eye region;

Figure 1:
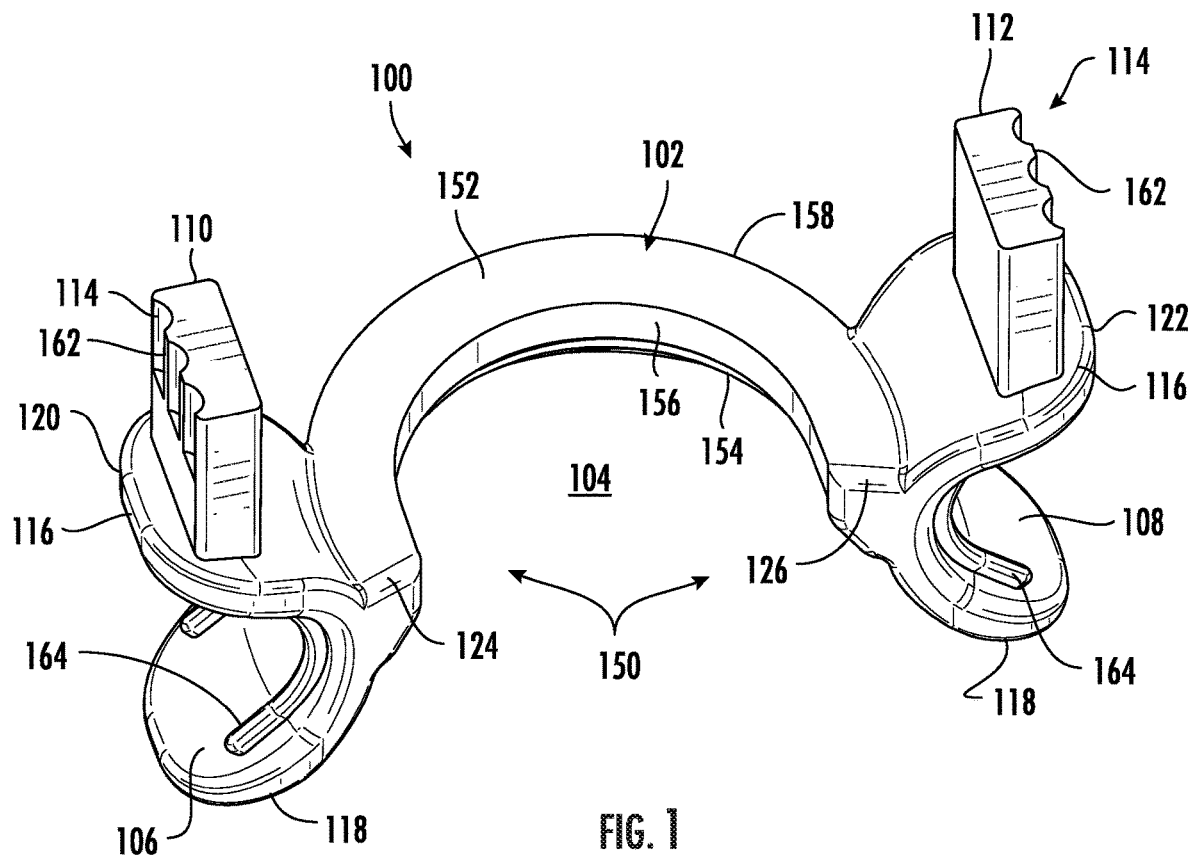
FIG. 1 is a perspective view of the eyelid speculum of the present invention.

Repeat use of reference characters in the present specification and drawings is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to an eyelid speculum, a kit containing the eyelid speculum, and a method of using the eyelid speculum in the diagnosis and/or treatment of a patient. The eyelid speculum includes a central ring having an upper surface, a lower surface, an inner side surface, an outer side surface, a first end, and a second end. The first end and the second end are separated by a gap, and the central ring defines an opening. The eyelid speculum also includes a first eyelid margin holder and a second eyelid margin holder that both extend outwardly from the outer surface of the central ring at the first end and second end, respectively, where each eyelid margin holder has an upper portion and a lower portion. In addition, the eyelid speculum includes finger tabs that extend upwardly from the upper portions of the first eyelid margin holder and the second eyelid margin holder.

Without intending to be limited by any particular theory, the present inventors have found that the particular features of the eyelid speculum of the present invention allow for the eyelid speculum to retract the eyelids and eyelashes adequately so that a health care provider can perform a desired diagnostic or treatment procedure on the eye (e.g., injections, imaging, and any other diagnostic or treatment procedures) with an unobstructed view and with minimized risk for contamination. Specifically, the eyelid speculum of the present invention is compact and sturdy yet comfortable to the patient, where the semicircular or c-shaped design of the central ring, where a gap is present between opposing ends of the ring and the central opening of the ring that allows for an unobstructed view of the portion of the eye being examined, imaged, injected, etc. In addition, the lid margin holds are curved such that they may form a c-shape or semicircular-shape, where the curved shape allows for the eyelid and eyelashes to be "scooped" into the eyelid margin holder and out of the health care provider's field of view when performing any variety of eye procedures. The shape of the eyelid margin holders also allows for the central ring to be anteriorly displaced from the outer surface of the eye (e.g., the corneal surface) so that the patient can still move his or her eye up and down and from side to side to, for instance, facilitate exposure of the injection site without the cornea contacting the eyelid speculum.

Further, the lid margin holders are spaced apart from each other by an angle θ that is defined as the angle between the first end and the second end of the central ring of the eyelid speculum, where the θ ranges from about 120° to about 185°, such as from about 125° to about 175°, such as from about 135° to about 165°. This particular angle range allows for the health care provider to accurately place the eyelid speculum for retraction of the eyelid and eyelashes, where if the angle was too small or too large, proper placement of the eyelid speculum in a location to retract both the eyelids would be challenging. Moreover, the finger tabs extending upwardly from the outer edge of the upper portion of each of the lid margin holders facilitate handling of the eyelid speculum in a safe and sterile manner. Thus, the eyelid speculum of the present invention allows for a more comfortable experience for the patient, while also allowing the health care provider to have an unobstructed view of the desired portions of the patient's eye for then conducting a diagnostic or treatment procedure.

In addition, the eyelid speculum can be formed from autoclavable and/or sterilizable materials that can also be disposable, thus eliminating the need to re-sterilize the eyelid speculum, which can increase the risk of a patient acquiring an infection. For instance, the eyelid speculum can be formed from a thermoplastic polymer. Although any suitable thermoplastic polymer can be used to form the eyelid speculum of the present invention, in one particular embodiment, the eyelid speculum and any accessories, attachments, etc. can be formed from acrylonitrile butadiene styrene, polyethylene, polypropylene, polycarbonate, polyamide, polystyrene, polymethyl methacrylate, or a combination thereof. In still other embodiments, the eyelid speculum and any accessories, attachments, etc. can be formed from any suitable biodegradable material. Moreover, it is to be understood that the eyelid speculum and any accessories, attachments, etc. can be formed via injection molding, 3D printing, thermomolding, or any other suitable method.

Various embodiments of the present invention will now be described in more detail.

Figure 2:
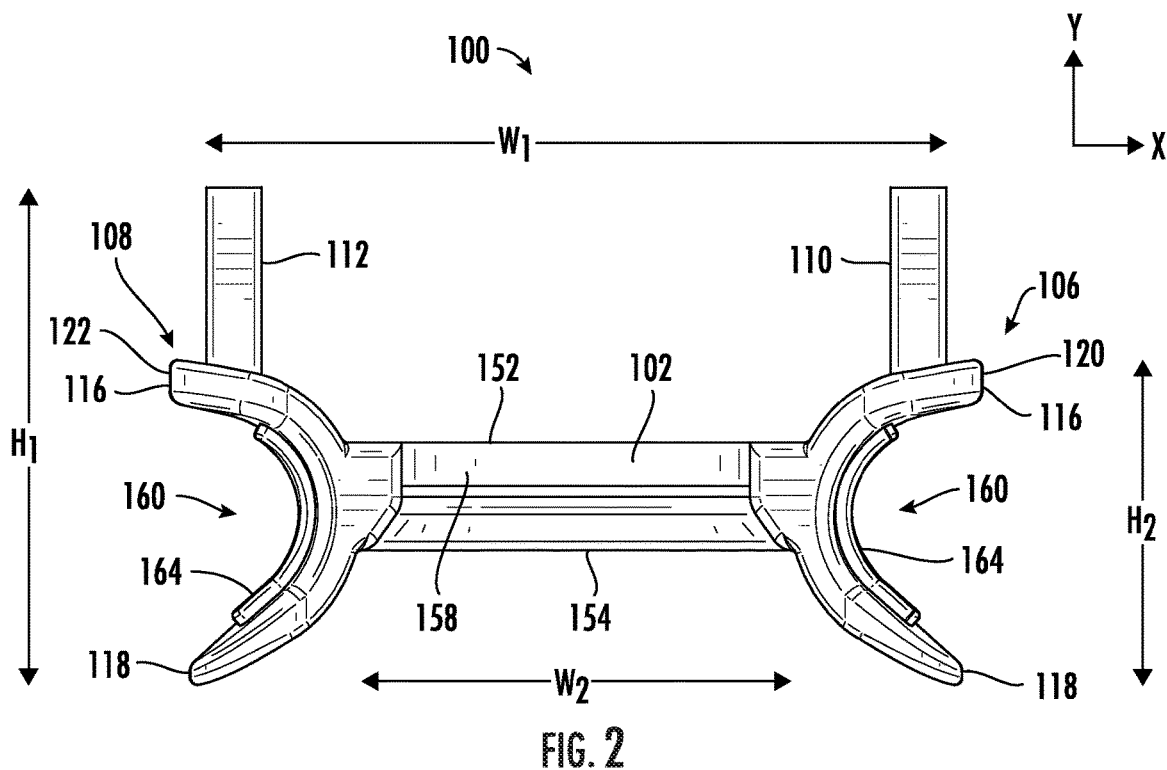
FIG. 2 is a front view of the eyelid speculum of the present invention.

Referring now to FIGS. 1-5, the particular components of the eyelid speculum 100 of the present invention are shown. Specifically, FIG. 1 is a perspective view of the eyelid speculum 100 of the present invention, FIG. 2 is a front view of the eyelid speculum 100 of the present invention, FIG. 3 is a top view of the eyelid speculum 100 of the present invention, FIG. 4 is a perspective view of another embodiment of the eyelid speculum of the present invention, and FIG. 5 is a side view of the eyelid speculum of the present invention. The eyelid speculum 100 includes a central ring 102 extending in a horizontal or x-direction and having an upper surface 152, a lower surface 154, an inner side surface 156, an outer side surface 158, a first end 124, and a second end 126. The first end 124 and the second end 126 are separated by a gap 150, and the central ring defines an opening 104, where such opening 104 allows a health care provider to have an unobstructed view of the desired portions of a patient's eye for then conducting any number of diagnostic and/or treatment procedures. The eyelid speculum 100 also includes a first eyelid margin holder 106 and a second eyelid margin holder 108 that both extend outwardly from the outer side surface 158 of the central ring at the first end 124 and the second end 126, respectively, where each eyelid margin holder 106, 108 has an upper portion 116 and a lower portion 118 that are separated by a central portion 160. Further, the central portion 160 of the first eyelid margin holder 106 and the central portion 160 of the second eyelid margin holder 108 each contact the outer side surface 158 of the central ring 102. As described above, the first lid margin holder 106 and the second lid margin holder 108 are spaced apart from each other by an angle θ that is defined as the angle between the first end 124 and the second end 126 of the central ring 102 of the eyelid speculum 100, where the θ ranges from about 120° to about 185°, such as from about 125° to about 175°, such as from about 135° about 165°. Additionally, the upper portions 116 and the lower portions 118 of the first lid margin holder 106 and the second lid margin holder 108 can be curved (e.g., c-shaped or semicircular) to form a scoop-like shape to easily hold a patient's eyelids and eyelashes when the eyelid speculum 100 is inserted into an eye of a patient.

In addition, the eyelid speculum 100 includes a first finger tab 110 and a second finger tab 112 that extend upwardly in the vertical or y-direction, for instance, next to or adjacent the outer edge 120 and the outer edge 122 of the upper portions 116 of the first eyelid margin holder 106 and the second eyelid margin holder 108. As shown in FIGS. 1 and 3, the first finger tab 110 and the second finger tab 112 can either be straight, or, in some embodiments (not shown), the first finger tab 110 and the second finger tab 112 can be curved (e.g., semicircular or c-shaped), where the curved-shape can correspond with the curved-shape of the outer edge 120 and the outer edge 122 of the upper portions 116 of the first eyelid margin holder 106 and the second eyelid margin holder 108. Further, the outer surface 114 of the finger tabs 110 and 112 can be textured to enable the health care provider to easily grasp the finger tabs 110 and 112 during insertion and rotation of the eyelid speculum 100. For example, the outer surface 114 can include a plurality of ridges 162 or any other suitable texturing means.

Although FIGS. 1-5 show one particular embodiment of the eyelid speculum 100 in terms of shape and size, it is to be understood that the eyelid speculum 100 can come in various shapes and sizes to treat newborns, infants, toddlers, young adults, adults, and even large animals (e.g., cows, horses, etc.). For instance, comparing FIG. 6A, which shows the eyelid speculum 100 of FIGS. 1-5 with FIG. 6B, it is appreciated by one of skill in the art that the size of the finger tabs 110 and 112, the size of the central ring 102, and the size of the first eyelid margin holder 106 and the second eyelid margin holder 108 can vary depending on the particular patient being diagnosed or treated (e.g., premature baby, infant, toddler, young adult, adult) and the particular procedure being conducted (e.g., injection, imaging, laser procedure, surgical procedure). Specifically, eyelid speculum 200 of FIG. 6B has smaller finger tabs 110 and 112 and a thinner central ring 102 compared to the eyelid speculum 100.

In addition, as shown in FIGS. 1, 2, and 4, the central portion 120 as well as the upper portion 116 and lower portion 118 of the first eyelid margin holder 106 and the second eyelid margin holder 108 can include one or more ridges 164. The ridges 164 help to maintain the eyelid speculum 100 in the proper position when being used on a patient by counteracting any movement of the eyelid speculum 100 that might be caused by a patient squeezing or trying to close his or her eyelids, which could lead to counter rotation and misalignment of the eyelid speculum 100. Without intending to be limited by any particular theory, the present inventors have found that the ridges 164 on the inner surfaces of the first eyelid margin holder 106 and the second eyelid margin holder 108 can prevent movement of the eyelid speculum 100 when aligned perpendicular to the direction of the eyelid movement.

In any event and referring to FIG. 2, the eyelid speculums 100 and 200 contemplated by the present invention can have an overall height $H_1$ in the vertical or y-direction ranging from about 0.2 inches (about 5.1 millimeters) to about 0.8 inches (about 20.3 millimeters), such as from about 0.3 inches (about 7.6 millimeters) to about 0.7 inches (about 17.8 millimeters), such as from about 0.4 inches (about 10.2 millimeters) to about 0.6 inches (about 15.2 millimeters). In addition, the distance between the upper portion 116 and the lower portion 118 of the first eyelid margin holder 106 and the distance between the upper portion 116 and the lower portion 118 of the second eyelid margin holder 108 can have a height $H_2$ in the vertical or y-direction ranging from about 0.15 inches (about 3.8 millimeters) to about 0.45 inches (about 11.4 millimeters), such as from about 0.2 inches (about 5.1 millimeters) to about 0.4 inches (about 10.2 millimeters), such as from about 0.25 inches (about 6.4 millimeters) to about 0.35 inches (about 8.9 millimeters). Moreover, the ratio of $H_1/H_2$ can range from about 1.25 to about 2.5, such as from about 1.5 to about 2.25, such as from about 1.75 to about 2.

Further, the eyelid speculums 100 and 200 can have an overall width $W_1$ in the horizontal or x-direction ranging from about 0.5 inches (about 12.7 millimeters) to about 1.75 inches (about 44.5 millimeters), such as from about 0.75 inches (about 19.1 millimeters) to about 1.5 inches (38.1 millimeters), such as from about 1 inch (about 25.4 millimeters) to about 1.25 inches (about 31.8 millimeters). In addition, the opening 104 defined by the central ring 102 can have a width $W_2$ in the horizontal or x-axis can range from about 0.25 inches (about 6.4 millimeters) to about 0.75 inches (about 19.1 millimeters), such as from about 0.35 inches (about 8.9 millimeters) to about 0.65 inches (about 16.5 millimeters), such as from about 0.45 inches (about 11.4 millimeters) to about 0.55 inches (about 14.0 millimeters). Additionally, the ratio of $W_1/W_2$ can range from about 1.5 to about 3, such as from about 1.75 to about 2.75, such as from about 2 to about 2.5.

Moreover, and referring to FIG. 5, the width $W_3$ of the eyelid margin holders 106 and 108 can range from about 0.1 inches (about 2.5 millimeters) to about 0.4 inches (about 10.2 millimeters), such as from about 0.15 inches (about 3.8 millimeters) to about 0.35 inches (about 8.9 millimeters), such as from about 0.2 inches (about 5.1 millimeters) to about 0.3 inches (about 7.6 millimeters). Further, the width $W_4$ of the finger tabs 110 and 112 can range from about 0.075 inches (about 1.9 millimeters) to about 0.3 inches (about 7.6 millimeters), such as from about 0.1 inches (about 2.5 millimeters) to about 0.25 inches (about 6.4 millimeters), such as from about 0.15 inches (about 3.8 millimeters) to about 0.2 inches (about 5.1 millimeters). In addition, the ratio of $W_3/W_4$ can range from about 1.1 to about 1.5, such as from about 1.2 to about 1.45, such as from about 1.3 to about 1.4.

Without intending to be limited by any particular theory, the present inventors have found that utilizing the particular height and width dimensions and ratios described balances the comfort of the patient with the ability of the health care provider to easily insert the eyelid speculums contemplated by the present invention.

Figure 7A:
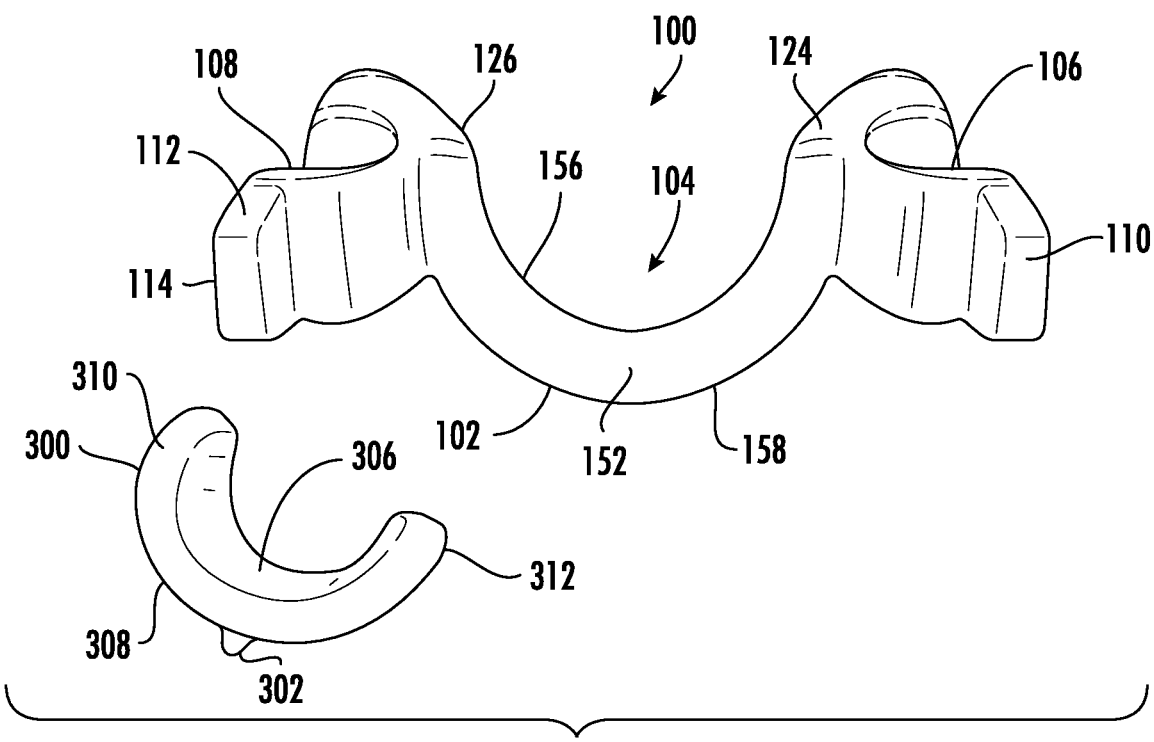
FIG. 7A is a perspective view of the eyelid speculum and accessory attachment of the present invention.
Figure 7B:
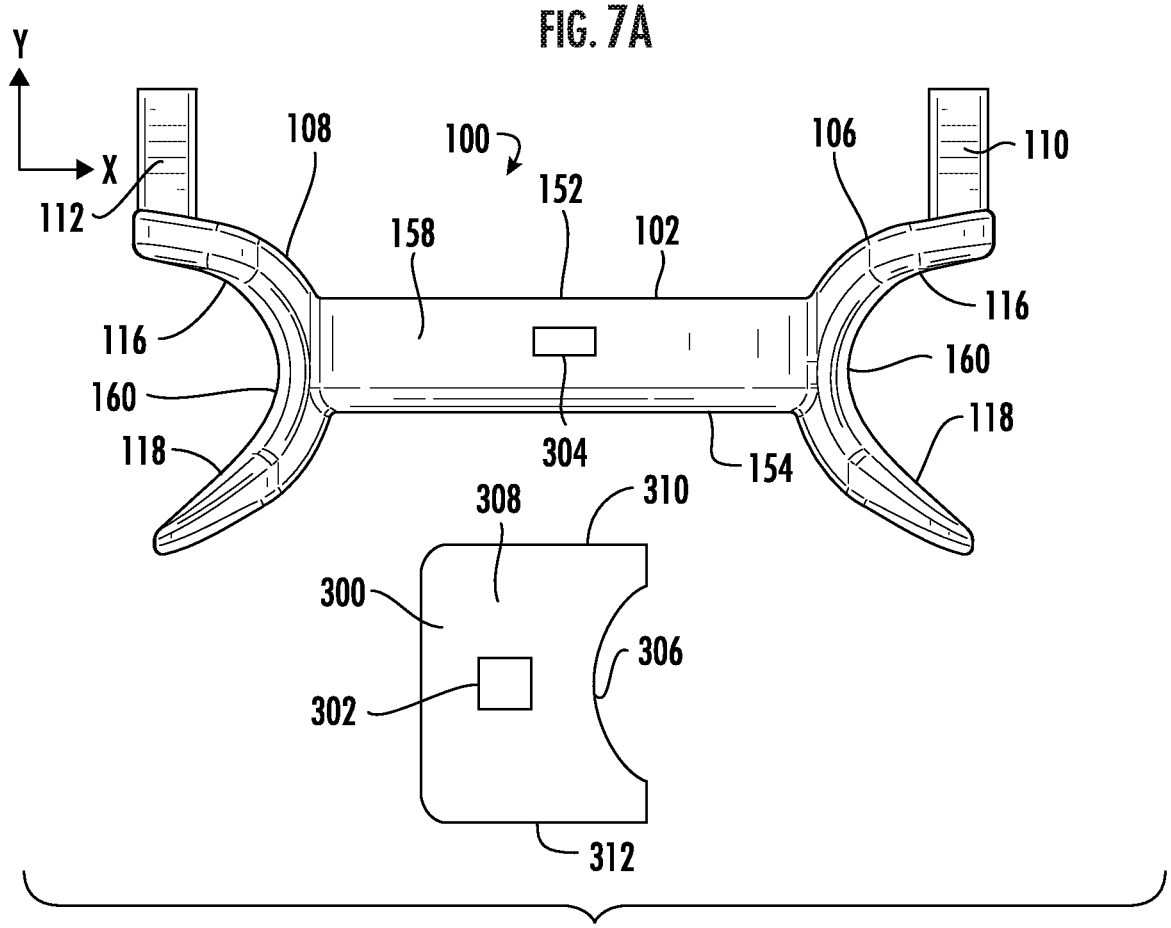
FIG. 7B is a front view of the eyelid speculum and accessory attachment of the present invention.
Figure 7C:
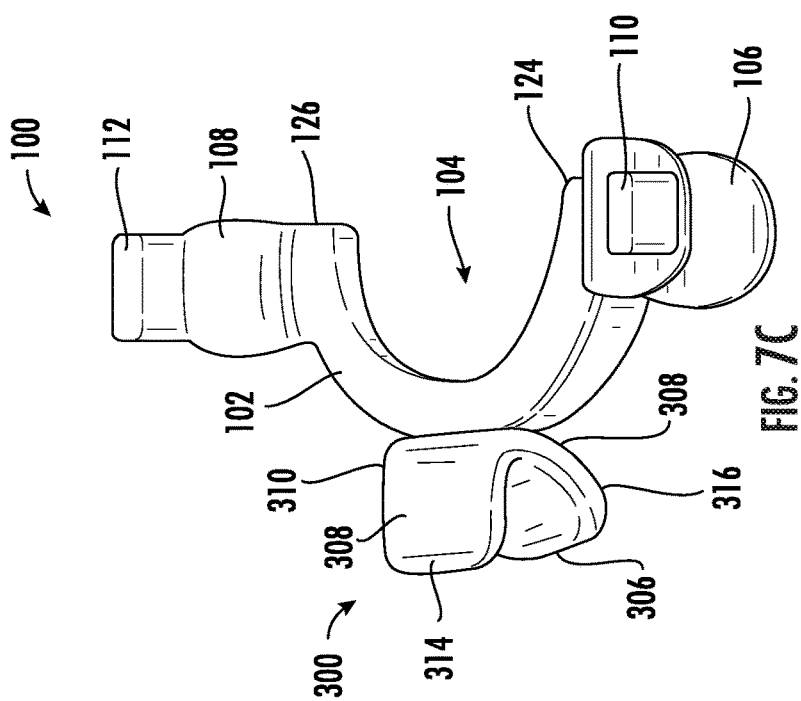
FIG. 7C is a side perspective view of the eyelid speculum and accessory attachment contemplated by the present invention.
Figure 11:
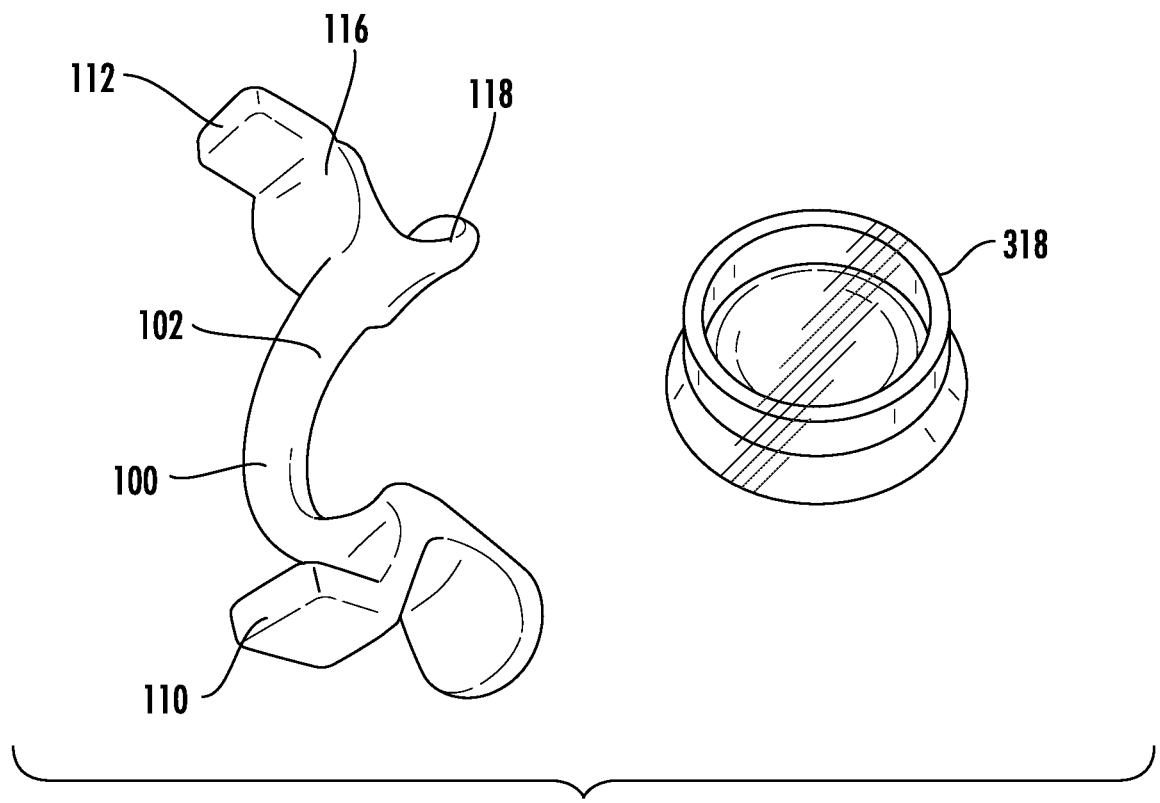
FIG. 11 is a system that includes the eyelid speculum of the present invention and a lens.
Figure 12:
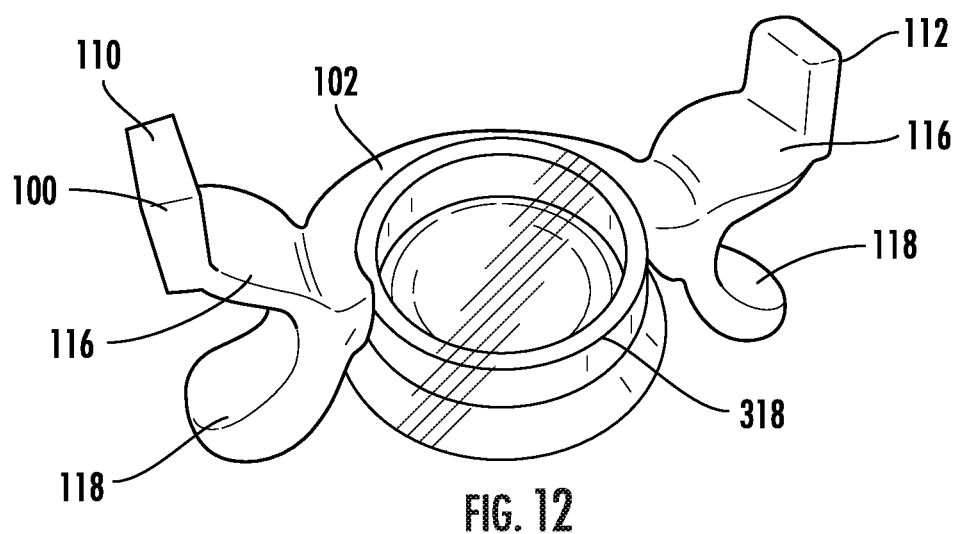
FIG. 12 shows the system of FIG. 11, where the lens is positioned within the opening defined by the central ring of the eyelid speculum.

Turning now to FIGS. 7A-7C, the present invention also contemplates that the eyelid speculum 100 can include one or more attachments 300 that can be positioned on the central ring 102 of the eyelid speculum 100. For instance, the central ring 102 can include a first mating component 304 and the attachment 300 can includes a second mating component 302, wherein central ring 102 and the attachment 300 can be connected to one another by the first mating 304 component and the second mating component 302. The first mating component 304 can be in the form of an indentation, socket, etc., while the second mating component 302 can be in the form of a protrusion, ball, etc. and vice versa. In any event, any suitable attachment mechanisms can be used to join the eyelid speculum 100 to the attachment 300, and when connected, the outer surface 308 of the attachment 300 can be positioned adjacent the outer side surface 158 of the central ring 102, and the first edge 310 and the second edge 312 of the attachment can be positioned between the first end 124 and the second end 126 of the central ring 102. Meanwhile, the attachment 300 can have a curved shape such that the inner surface 306 of the attachment 300 can be defined by upper portion 314 and lower portion 316 of the attachment. The attachment 300 can be used in conjunction with the eyelid speculum 100 during certain procedures such as anterior chamber paracentesis, where the health care provider can press on the attachment 300 with a finger, such as at its upper portion 316, to indirectly press on the eye, stabilize the eye globe during insertion of a needle into the anterior chamber, and help express fluid into a needle inserted in the anterior chamber between the cornea and iris. Thus, the present invention is directed to not only the eyelid speculum 100 described above, but also various accessories such as the attachment 300 discussed above, or any other accessory that can be attached to the eyelid speculum 100 to assist a health care provider in performing a diagnostic or treatment procedure. For instance, accessories such as attachment 300 can be used not only for anterior chamber paracentesis, but can also be used during removal of corneal foreign bodies, surgical lens placement, imaging, vitrectomy viewing, etc. For example, and referring to FIGS. 11 and 12, the eyelid speculum 100 can be used for placement of a surgical lens 318, where the surgical lens 318 can be placed within the opening 104 and can be designed so that the perimeter of the surgical lens 318 has the same curvature as the central ring 102.

Figure 8A:
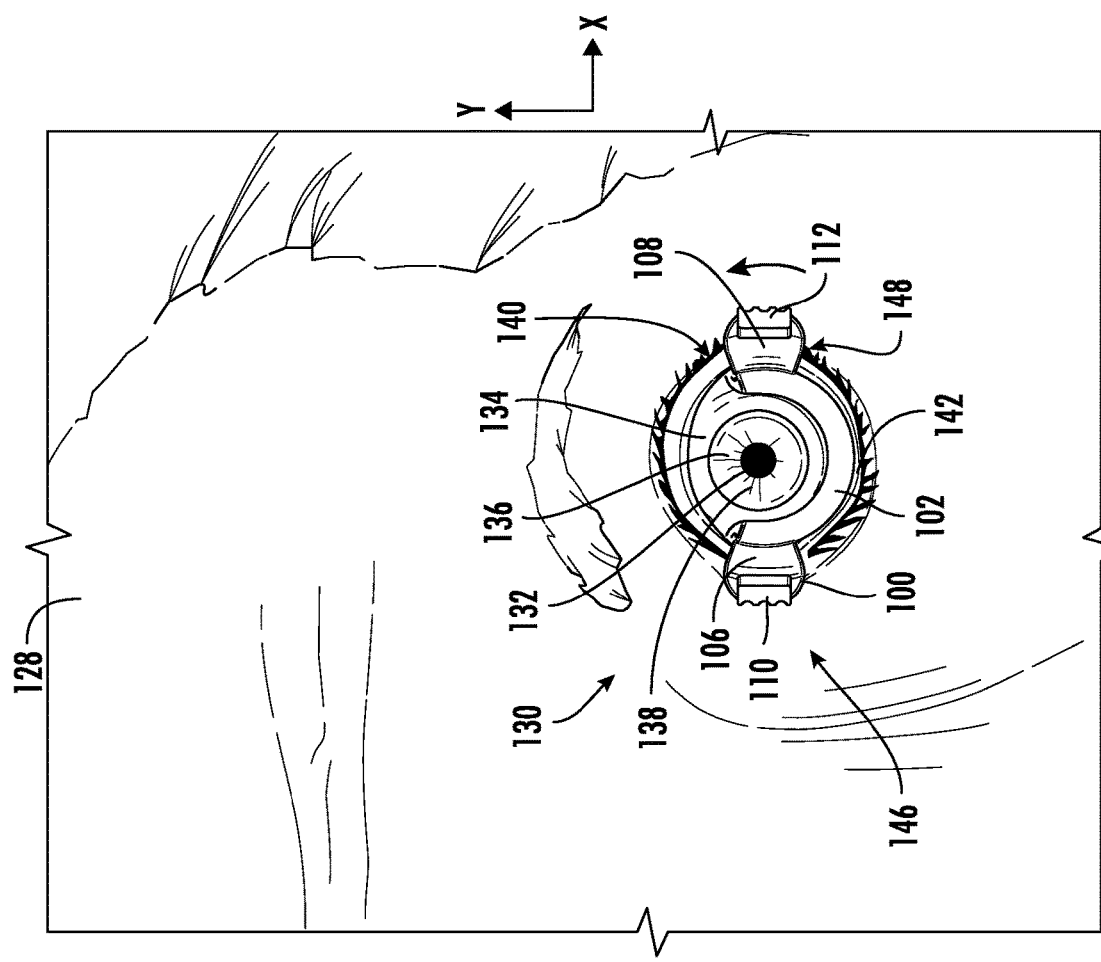
FIG. 8A illustrates the eyelid speculum of the present invention as it is first being inserted into an eye region of patient.
Figure 9:
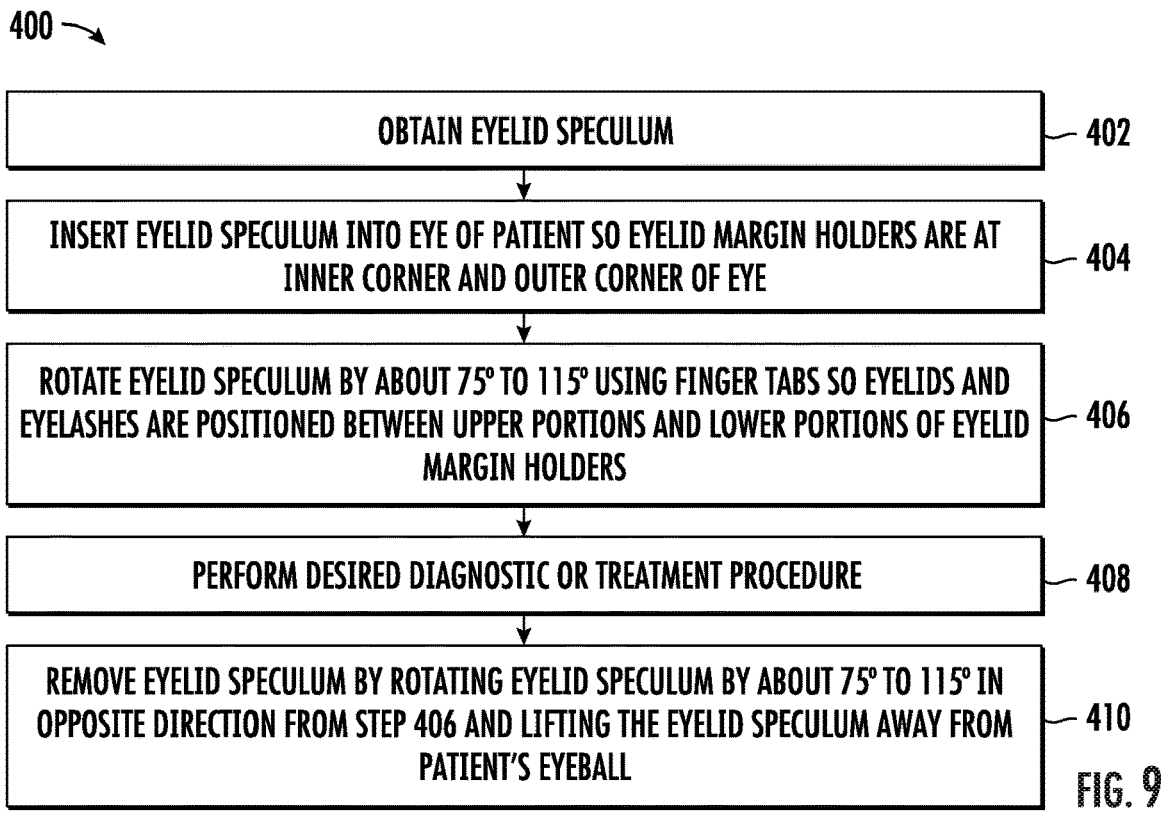
FIG. 9 is a block diagram illustrating one method of using the eyelid speculum of the present invention.

Referring now to FIGS. 8A-9, one method 400 for using the eyelid speculum 100 of the present invention to retract the eyelids of a patient is described in more detail. Generally, the method 400 for separating a first eyelid 140 (e.g., the upper eyelid) and a second eyelid 142 (e.g., lower eyelid) as well as the eyelashes 144 of a patient 128 from an outer surface 138 (e.g., the corneal surface covering the pupil 132 and iris 136 of an eye 130 and continuous with the sclera 134) of the eye 130 includes obtaining an eyelid speculum in step 402, and then inserting the eyelid speculum into an eye of a patient in step 404, where the lower surface 154 of the central ring 102 of the eyelid speculum 100 is positioned adjacent yet does not contact the outer surface 138 of the eye 130, wherein the first eyelid margin holder 106 is positioned at an inner corner 146 of the eye 130 and the second eyelid margin holder 108 is positioned at an outer corner 148 of the eye 130. Such initial positioning is shown in FIG. 8A for a left eye 130 of a patient 128, although it is to be understood that similar positioning would be used for the right eye.

Next, in step 406, a health care provider can rotate the eyelid speculum 100 by about 75° to about 115° of a 360° circle, such as from about 80° to about 110°, such as from about 85° to about 105° via the finger tabs 110 and 112 so that the upper eyelid 140 as well as at least a portion of the patient's eyelashes 144 extending from the upper eyelid 140 are positioned between the upper portion 116 and lower portion 118 of the first eyelid margin holder 106 and so that the lower eyelid 142 as well as at least a portion of the patient's eyelashes 144 extending from the lower eyelid 142 are positioned between the upper portion 116 and lower portion 118 of the second eyelid margin holder 108, as shown in FIG. 8B. When placing the eyelid speculum 100 in the left eye, the eyelid speculum 100 can be rotated in the counterclockwise direction, and when placing the eyelid speculum in the right eye, the eyelid speculum 100 can be rotated in the clockwise direction. However, it is also to be understood that when placing the eyelid speculum 100 in the left eye, the eyelid speculum 100 can be rotated in the clockwise direction, and when placing the eyelid speculum in the right eye, the eyelid speculum 100 can be rotated in the counterclockwise direction, and the direction of rotation can depend upon the anatomical location of the eye that the healthcare provider needs access to for performing a specific diagnostic or treatment procedure.

Additionally, after inserting the eyelid speculum 100 into the eye 130 of the patient 128 as shown in FIGS. 8A and 8B, the patient 128 is still able to move his or her eye 130 in the medial M or lateral L direction as shown in FIG. 8C since the central ring 102 is free from contact with the outer surface 138 of the eye 130. This feature of the eyelid speculum 100 allows for a more comfortable experience for the patient 128 and also provides more options for the healthcare provider in performing any diagnostic or treatment procedures since the patient 128 is able to move his or her eye 130, as shown in step 408.

Next, after the desired diagnostic or treatment procedure has been performed, the eyelid speculum 100 can be removed in step 410 by rotating the eyelid speculum 100 by about 75° to about 115° of a 360° circle, such as from about 80° to about 110°, such as from about 85° to about 105° via the finger tabs 110 and 112 in a direction opposite from the direction of rotation of insertion in step 404 such that the first eyelid margin holder 106 is positioned at an inner corner 146 of the eye 130 and the second eyelid margin holder 108 is positioned at an outer corner 148 of the eye 130 and lifting the eyelid speculum 100 away from the outer surface 138 of the eye 130. For instance, if the eyelid speculum 100 was inserted by rotating the eyelid speculum 100 in the counterclockwise direction, then removal of the eyelid speculum 100 would involve rotating the eyelid speculum 100 in the clockwise direction. Meanwhile, if the eyelid speculum 100 was inserted by rotating the eyelid speculum 100 in the clockwise direction, then removal of the eyelid speculum 100 would involve rotating the eyelid speculum 100 in the counterclockwise direction. After removal, the eyelid speculum 100 can be disposed of or recycled since it can be economically fabricated from a thermoplastic polymer for one-time or single use. Such a method 400 as described in FIG. 9 is simple and efficient for the healthcare provider and safe for the patient and avoids the use of the bulky, metal conventional eyelid speculums known in the art.

Figure 10:
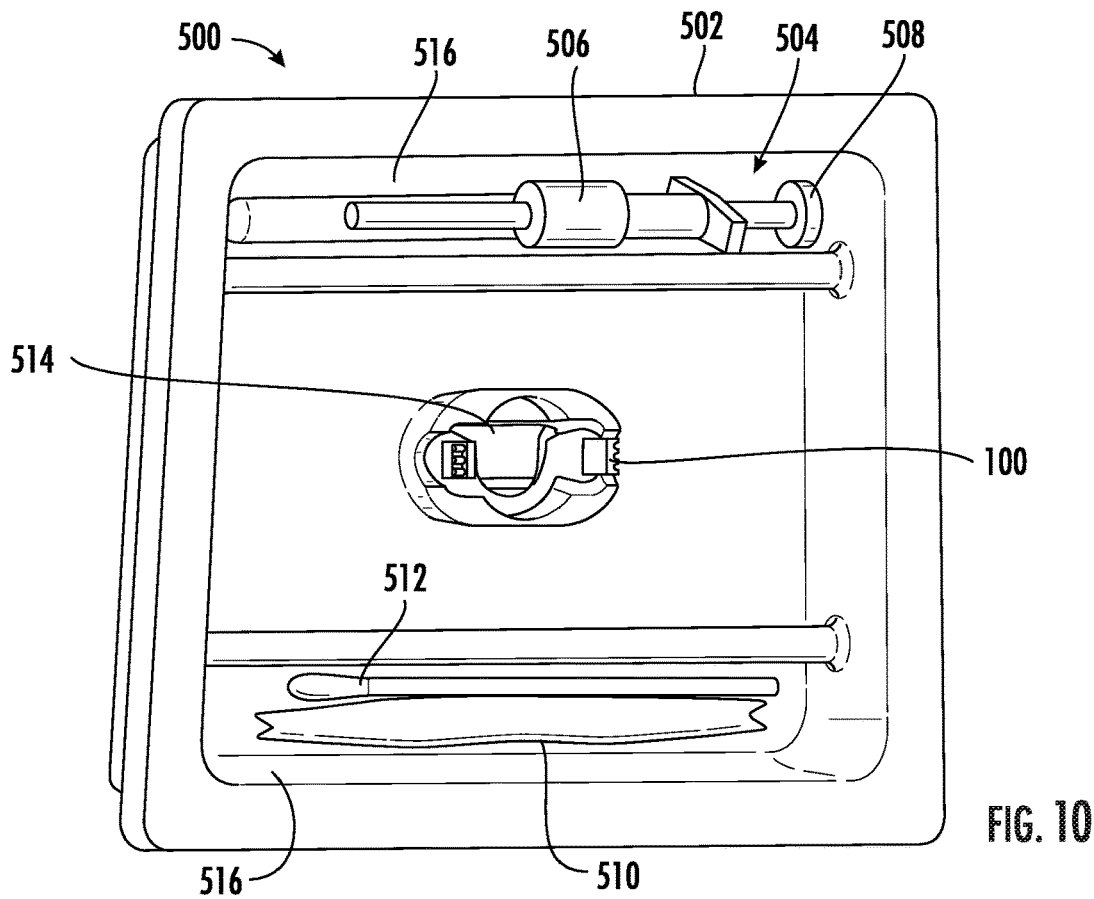
FIG. 10 is a kit that includes the eyelid speculum of the present invention.

Referring now to FIG. 10, the eyelid speculum 100 of the present invention can be a part of a kit 500 that can be provided to the healthcare provider in a sterile package 502 depending on the diagnostic or treatment procedure to be performed. For instance, the package 502 can include the eyelid speculum 100 and a medication delivery system 504 such as a needle/syringe 508, dropper, etc. and medication 506. In addition, it is to be understood that in place of or in addition to the medication delivery system 504, the kit 500 can also include one or more medical instruments 510, cotton swabs 512, and other supplies such as but not limited to measuring devices, disinfecting solutions (i.e., betadine), and/or any other medical supply that the healthcare provider would typically need to perform the desired diagnostic or treatment procedure. Further, as shown, the eyelid speculum 100 can be positioned within a recess 514 for easy access by the health care provider and to ensure the health care provider removes the eyelid speculum 100 from the package 502 in the proper orientation.

Further, it is to be understood that the eyelid speculum 100 is contemplated for use in humans as well as other animals, including, but not limited to canines, felines, bovines, and equines.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An eyelid speculum comprising:
a central ring having an upper surface, a lower surface, an inner side surface, an outer side surface, a first end, and a second end, wherein the first end and the second end are separated by a gap, and wherein the central ring defines an opening;
a first eyelid margin holder extending outwardly from the outer side surface of the central ring at the first end and having an upper portion and a lower portion;
a second eyelid margin holder extending outwardly from the outer side surface of the central ring at the second end and having an upper portion and a lower portion;
a first finger tab extending upwardly from the upper portion of the first eyelid margin holder, wherein the first finger tab is located adjacent an outer edge of the upper portion of the first eyelid margin holder; and
a second finger tab extending upwardly from the upper portion of the second eyelid margin holder, wherein the second finger tab is located adjacent an outer edge of the upper portion of the second eyelid margin holder.

2. The eyelid speculum of claim 1, wherein an angle formed between the first end and the second end ranges from about 120° to about 185°.

3. The eyelid speculum of claim 1, wherein the central ring is c-shaped or semicircular.

4. The eyelid speculum of claim 1, wherein the first eyelid margin-holder and the second eyelid margin holder are c-shaped or semicircular.

5. The eyelid speculum of claim 1, wherein the upper portions and the lower portions of the first eyelid margin holder and the second eyelid margin holder extend from the outer side surface of the central ring.

6. The eyelid speculum of claim 1, wherein the upper portions and the lower portions of the first eyelid margin holder and the second eyelid margin holder are curved.

7. The eyelid speculum of claim 1, wherein the upper portion and the lower portion of the first eyelid margin holder are separated by a central portion, and wherein the upper portion and the lower portion of the second eyelid margin holder are separated by a central portion.

8. The eyelid speculum of claim 7, wherein the central portion of the first eyelid margin holder and the central portion of the second eyelid margin holder each contact the outer side surface of the central ring.

9. The eyelid speculum of claim 1, wherein the first finger tab and the second finger tab each include a textured outer surface.

10. The eyelid speculum of claim 9, wherein the textured outer surface comprises a plurality of ridges.

11. The eyelid speculum of claim 1, wherein the first eyelid margin holder is configured for positioning around an upper eyelid and the second eyelid margin holder is configured for positioning around a lower eyelid.

12. The eyelid speculum of claim 1, wherein the central ring is free from contact with an outer surface of an eye of a patient when the eyelid speculum is used to retract an eyelid of the patient.

13. The eyelid speculum of claim 1, wherein the eyelid speculum is formed from a thermoplastic polymer.

14. The eyelid speculum of claim 13, wherein the thermoplastic polymer comprises acrylonitrile butadiene styrene, polyethylene, polypropylene, polycarbonate, polyamide, polystyrene, polymethyl methacrylate, or a combination thereof.

15. The eyelid speculum of claim 1, wherein the eyelid speculum is disposable after a single use.

16. The eyelid speculum of claim 1, further comprising an attachment, wherein the central ring includes a first mating component and the attachment includes a second mating component, wherein central ring and the attachment are connected by the first mating component and the second mating component.

17. A kit comprising the eyelid speculum of claim 1 and a medication delivery system.

18. The kit of claim 17, wherein the eyelid speculum and the medication delivery system are contained within a sterilized package.

19. The kit of claim 17, further comprising a medication.

20. A method for separating a first eyelid and a second eyelid from an outer surface of an eye of a patient, the method comprising:
  inserting the eyelid speculum of claim 1 into the eye of the patient, wherein the lower surface of the central ring is positioned adjacent yet does not contact the outer surface of the eye, wherein the first eyelid margin holder is positioned at an inner corner of the eye and the second eyelid margin holder is positioned at an outer corner of the eye; and
  rotating the eyelid speculum in a first direction by about 75° to about 115° via the first finger tab and the second finger tab by about 75° to about 115° such that the first eyelid is positioned between the upper portion and the lower portion of the first eyelid margin holder and the second eyelid is positioned between the upper portion and the lower portion of the second eyelid margin holder.

21. The method of claim 20, further comprising:
performing a desired diagnostic or treatment procedure; and
removing the eyelid speculum by rotating the eyelid speculum in a second direction that is opposite the first direction by about 75° to about 115° via the first finger tab and the second finger tab such that the first eyelid margin holder is positioned at an inner corner of the eye and the second eyelid margin holder is positioned at an outer corner of the eye and lifting the eyelid speculum away from the outer surface of the eye.

* * * * *